United States Patent
Wehrli

[11] Patent Number: 5,905,153
[45] Date of Patent: May 18, 1999

[54] PROCESS FOR PREPARING (9α,13α,14α)-1-(3-METHOXY-MORPHINAN-17-YL) ALKANONES

[75] Inventor: Christof Wehrli, Witterswil, Switzerland

[73] Assignee: Roche Vitamins Inc., Parsippany, N.J.

[21] Appl. No.: 08/923,371

[22] Filed: Sep. 3, 1997

[30] Foreign Application Priority Data

Oct. 2, 1996 [EP] European Pat. Off. ............ 96115783

[51] Int. Cl.⁶ .................................................. C07D 221/28
[52] U.S. Cl. ............................................................. 546/74
[58] Field of Search ................................................. 546/74

[56] References Cited

U.S. PATENT DOCUMENTS

| | | | |
|---|---|---|---|
| 3,634,429 | 1/1972 | Leimgruber et al. | 546/74 |
| 3,810,899 | 5/1974 | Mohacsi et al. | 546/74 |
| 3,914,232 | 10/1975 | Mohacsi et al. | 546/74 |
| 3,914,233 | 10/1975 | Mohacsi et al. | 546/74 |
| 3,914,234 | 10/1975 | Mohacsi et al. | 546/74 |
| 4,857,648 | 8/1989 | Broger et al. | 546/147 |

FOREIGN PATENT DOCUMENTS

| | | |
|---|---|---|
| 1584396 | 12/1969 | France . |
| 2311 881 | 9/1973 | Germany . |

OTHER PUBLICATIONS

Derwent Abstract of Japanese Patent Publication 01034964 (1997).

Kitamura et al., "General Asymetric Synthesis of Benzomorphans and Morphinans via Enantioselective Hydrogenation", Tetrahedron Letters, vol. 28, No. 41, pp. 4829–4832 (1987).

Schnider et al., "Synthesis of Morphinan", Helv. Chim Acta, 33:1437–1448 (1950).

*Primary Examiner*—Alan L. Rotman
*Attorney, Agent, or Firm*—George W. Johnston; Dennis P. Tramaloni

[57] ABSTRACT

(9α, 13α,14α)-1-(3-Methoxymorphinan-17-yl)alkanones of the formula

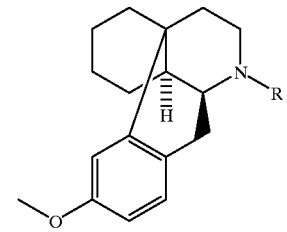

I wherein R signifies lower alkanoyl, are valuable intermediates for the manufacture of dextromethorphan of the formula

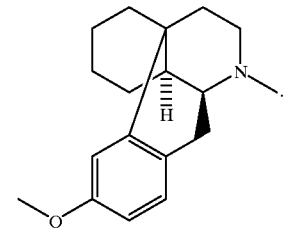

III

They can be produced in an advantageous manner by cyclization of a (R)- or (S)-1-[1-(4-methoxybenzyl)-1,2,3,4,5,6,7,8-octahydro-isoquinolin-2-yl]alkanone of the formula

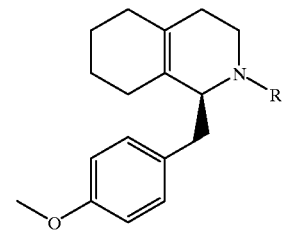

II with an alkylsulfonic acid or a mixture of alkylsulfonic acids at a temperature between about 5° and 50° C., but above the melting point of the alkylsulfonic acid used or of the alkylsulfonic acid mixture used, and can be converted into dextromethorphan in a manner known per se by cleavage or the residue R and N-methylation.

9 Claims, No Drawings

PROCESS FOR PREPARING (9α,13α,14α)-1-(3-METHOXY-MORPHINAN-17-YL) ALKANONES

BACKGROUND

Various processes for the manufacture of dextromethorphan are already known. One such process is described, for example, in Helv. Chim. Acta 33, 1437 (1950). According to this known process (R)- or (S)-1-[1-(4-methoxybenzyl)-2-methyl-1,2,3,4,5,6,7,8-octahydro-isoquinoline is cyclized with phosphoric acid in 66% yield. The low yield in the final step is a disadvantage of this process.

Another starting material, (R)- or (S)-1-[1-(4-methoxybenzyl)-2-formyl-1,2,3,4,5,6,7,8-octahydro-isoquinoline, as well as its conversion into dextromethorphan is known from Tetrahedron Letters (1987), 28, 4829 and, respectively, Japanese Patent Publication 01034964, although no details with respect to yield are present. This is not important, since this conversion is not particularly attractive. In particular, (R)- or (S)-1-[1-(4-methoxybenzyl)-2-formyl-1,2,3,4,5,6,7,8-octahydro-isoquinoline has to be produced either by racemate resolution (yield≦50%) from rac. 1-[1-(4-methoxybenzyl)-1,2,3,4,5,6,7,8-octahydro-isoquinoline and subsequent N-formylation or according to the two references given above by asymmetric hydrogenation from (Z)-1-[1-(4-methoxybenzylidene)-1,2,3,4,5,6,7,8-octahydro-isoquinolin-2-yl]methanone which is accessible only in a complicated manner. The development of an enantioselective hydrogenation of (Z)-1-[1-(4-methoxybenzylidene)-1,2,3,4,5,6,7,8-octahydro-isoquinolin-2-yl]alkanones later opened up a simpler route for the production of (R)- or (S)-1-[1-(4-methoxybenzyl)-1,2,3,4,5,6,7,8-octahydro-isoquinolin-2-yl]alkanones without racemate resolution, see e.g. U.S. Pat. No. 4,857,648.

SUMMARY OF THE INVENTION

The present invention is concerned with a process for the production of (9α,13α,14α)-1-(3-methoxymorphinan-17-yl)alkanones of the formula

I

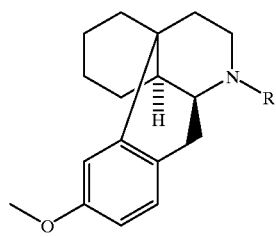

wherein R signifies lower alkanoyl, by the cyclization of a (R) or (S)-1-[1-(4-methoxybenzyl)-1,2,3,4,5,6,7,8-octahydro-isoquinolin-2-yl]alkanone of the formula

II

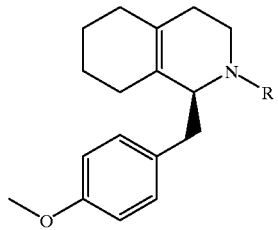

wherein R has the significance given above, with an alkylsulfonic acid.

The term "lower alkanoyl" used in this description signifies not only straight-chain but also branched residues of an aliphatic carboxylic acid with 2–4 carbon atoms, such as acetyl, propionyl, butyryl, and the like, with acetyl being especially preferred.

The (9α,13α,14α)-1-(3-methoxymorphinan-17-yl) alkanones of formula I above are important starting materials for the manufacture of dextromethorphan of the formula

III

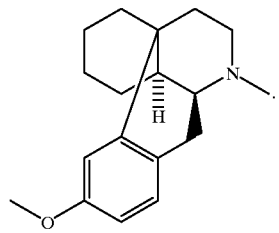

They can be converted into dextomethorphan in a known manner, for example, in analogy to the methods described in German Offenlegungsschrift 2 311 881 by cleavage of the residue R and N-methylation.

The object of the present invention is accordingly to provide a process for the production of (9α,13α,14α)-1-(3-methoxymorphinan-17-yl)alkanones of formula I above by the cyclization of a (R)- or (S)-1-[1-(4-methoxybenzyl)-1, 2,3,4,5,6,7,8-octahydro-isoquinolin-2-yl]alkanone of formula II above, which allows the cyclization of a meanwhile readily accessible (R)- or (S)-1-[1-(4-methoxybenzyl)- 1,2, 3,4,5,6,7,8-octahydro-isoquinolin-2-yl] alkanone in good yields. The use of the (9α,13α,14α)-1-(3-methoxymorphinan-17-yl)alkanones for the manufacture of dextromethorphan is also an object of the present invention.

DETAILED DESCRIPTION OF THE INVENTION

The objects of the present invention have been achieved by carrying out the cyclization using an alkylsulfonic acid or a mixture of alkylsufonic acids under the specific reaction conditions described below in detail.

Accordingly, the present invention is concerned with a process for the production of (9α,13α,14α)-1-(3-methoxymorphinan-17-yl)alkanones of formula I above, which process comprises cyclizing a (R)- or (S)-1-[1-(4-methoxybenzyl)-1,2,3,4,5,6,7,8-octahydro-isoquinolin-2-yl]alkanone of formula II above with an alkylsulfonic acid or a mixture of alkylsulfonic acids at a temperature between about 5° C. and 50° C., but above the melting point of the alkylsulfonic acid used or of the alkylsulfonic acid mixture used, preferably between about 10° C. and room temperature.

The cyclization of a (R)- or (S)-1-[1-(4-methoxybenzyl)-1,2,3,4,5,6,7,8-octahydro-isoquinolin-2-yl]alkanone is carried out in a known manner in the acid used, whereby this simultaneously also serves as the solvent. An alkylsufonic acid or a mixture of alkylsulfonic acids, especially methane-, ethane- and propanesulfonic acid, particularly methanesulfonic acid, is suitable for the purpose of the present invention. When the respective alkylsulfonic acids are solid at the preferred reaction temperatures between about 10° C. and room temperature and these can therefore not simultaneously serve as the solvent, it is necessary to lower the melting point of the acid(s) by the addition of 0–4%, preferably 0–2%, water or by admixture of another alkylsulfonic acid such that the reaction can be carried out above the melting point of the acid or of the acid mixture. When >1% of water is added, the speed at which the educt reacts decreases somewhat, although the yield can be held constant using an appropriately longer reaction time.

The (R)- or (S)-1-[1-(4-methoxybenzyl)-1,2,3,4,5,6,7,8-octahydro-isoquinolin-2-yl]alkanone is advantageously added in molten form (at about 85° C.) to the cold acid. The (9α,13α,14α)-1-(3-methoxymorphinan-17-yl)alkanone is either crystallized directly from the acid by the addition of water at 60–65° C. or, after dilution with water, extracted with an organic solvent which is inert under the reaction conditions, such as toluene or methylene chloride, preferably toluene.

The compounds of formula II are known, for example, from U.S. Pat. No. 4,857,648, incorporated herein by reference, or can be prepared in a known manner.

The following Examples for the production of (9α,13α,14α)-1-(3-methoxymorphinan-17-yl)ethanone by the cyclization of (R)- or (S)-1-[1-(4-methoxybenzyl)-1,2,3,4,5,6,7,8-octahydro-isoquinolin-2-yl]ethanone illustrate especially advantageous embodiments of the process in accordance with the invention, but they do not represent any limitation. All temperatures are given in degrees Celsius.

EXAMPLE 1

200 g of anhydrous methanesulfonic acid were placed under an inert gas atmosphere in a 750 ml four-necked flask provided with a thermometer and paddle stirrer and treated with 2 ml of water. 30.40 g (100 mmol) of molten (heated to about 85° C.) (R)- or (S)-1-[1-(4-methoxybenzyl)-1,2,3,4,5,6,7,8-octahydro-isoquinolin-2-yl]ethanone (content: about 98%) were added to this solution in 4 portions within 30 minutes at a temperature of about 10–15°. The reaction mixture was stirred in a water bath. The (R)- or (S)-1-[1-(4-methoxybenzyl)- 1,2,3,4,5,6,7,8-octahydro-isoquinolin-2-yl]ethanone had dissolved completely after about 3 hours. The brown solution was stirred at 10–21° C. for 6 days. The course of the reaction was checked by gas chromatography.

| Reaction time [h] | Temperature [° C.] | Conversion [%] |
|---|---|---|
| 0 | 10° | 0 |
| 24 | 12° | 25 |
| 48 | 14° | 55 |
| 72 | 17° | 78 |
| 96 | 20° | 89 |
| 120 | 21° | 98 |
| 144 | 21° | 99.5 |

EXAMPLE 2

400 ml of toluene and in one portion a mixture of 150 g of ice and 330 ml of water were added to the brown solution from Example 1. After stirring for 5 minutes the mixture was extracted with 2×100 ml of toluene. The toluene phases were washed in succession with 2×100 ml of water. The aqueous phases were combined and the methanesulfonic acid was recovered therefrom. The toluene phases were combined and evaporated in a water-jet vacuum. There were obtained 30.25 g (92%) of crude (9α,13α,14α-1-(3-methoxymorphinan-17-yl)ethanone, content according to GC: 91%.

EXAMPLE 3

600 ml of water were added dropwise at 60° while stirring within about 1 hour to the brown solution from Example 1. The crystal suspension obtained was cooled to room temperature. The solid was filtered of under suction, pressed out well and rinsed with 100 ml of water. The filter cake was dried at 35° in a water-jet vacuum for 18 hours. There were thus obtained 27.81 g (88%) of (9α,13α,14α)-1-(3-methoxymorphinan-17-yl)ethanone, content according to GC: 95%.

I claim:

1. A process for the production of (9α,13α,14α)-1-(3-methoxymorphinan-17-yl)alkanones of the formula

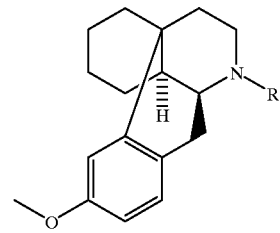

I wherein R signifies lower alkanoyl, which process comprises cyclizing a (R)- or (S)-1-[1-(4-methoxybenzyl)-1,2,3,4,-5,6,7,8-octahydro-isoquinolin-2-yl]alkanone of the formula

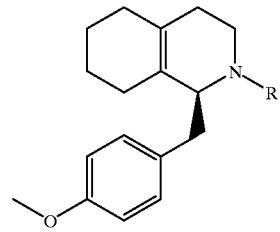

II wherein R has the significance given above, with an alkylsulfonic acid or a mixture of alkylsulfonic acids at a temperature between about 5° C. and 50° C., but above the melting point of the alkylsulfonic acid used or of the alkylsulfonic acid mixture used.

2. A process according to claim 1, wherein the alkylsulfonic acid is methane-, ethane- or propanesulfonic acid.

3. A process according to claim 1, wherein the alkylsulfonic acid is methanesulfonic acid.

4. A process according to claim 1, wherein the cyclization is carried out at a temperature between about 10° C. and room temperature.

5. A process according to claim 1, further comprising lowering the melting point of the alkylsulfonic acid is by the addition of 1–4% of water.

6. A process according to claim 5, wherein the melting point of the alkylsulfonic acid is lowered by the addition of 1–2% of water.

7. A process according to claim 1, further comprising lowering the melting point of the alkylsulfonic acid by admixture of another alkylsulfonic acid.

8. A process according to claim 1, comprising adding a molten form of the (R)- or (S)-1-[1-(4-methoxybenzyl)-1,2,3,4,5,6,7,8-octahydro-isoquinoline to a cold form of the acid.

9. A process for the manufacture of dextromethorphan of the formula

III

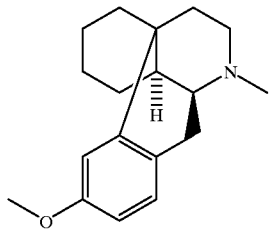

which process comprises (a) cyclizing a (R)- or (S)-1-[1-(4-methoxybenzyl)-1,2,3,4,5,6,7,8-octahydro-isoquinolin-2-yl]alkanone of the formula

II

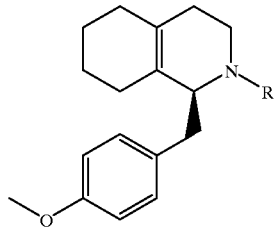

wherein R signifies lower alkanoyl, with an alkylsulfonic acid or a mixture of alkylsufonic acids at a temperature between about 5° C. and 50° C., but above the melting point of the alkylsulfonic acid used or of the alkylsufonic acid mixture used, and (b) converting the resulting (9α,13α,14α)-1-(3-methoxymorphinan-17-yl)alkanone of the formula

I

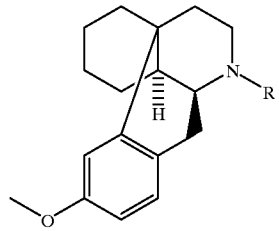

wherein R has the significance given above, into dextromethorphan by cleavage of the residue R and N-methylation.

* * * * *